United States Patent
Macklin et al.

(10) Patent No.: US 7,936,265 B2
(45) Date of Patent: May 3, 2011

(54) SMART CARD DETECTORS

(75) Inventors: Jon D. Macklin, El Cajon, CA (US); Walter C. Bonneau, Jr., Escondido, CA (US); Raymond DeKozan, La Mesa, CA (US); Joseph V J Ravenis, San Diego, CA (US); Bruce D. Roberts, San Diego, CA (US)

(73) Assignee: Cubic Corporation, San Diego, CA (US)

( * ) Notice: Subject to any disclaimer, the term of this patent is extended or adjusted under 35 U.S.C. 154(b) by 103 days.

(21) Appl. No.: 12/123,387

(22) Filed: May 19, 2008

(65) Prior Publication Data

US 2009/0115605 A1 May 7, 2009

Related U.S. Application Data

(60) Provisional application No. 60/938,677, filed on May 17, 2007.

(51) Int. Cl.
G08B 21/00 (2006.01)

(52) U.S. Cl. ..... 340/540; 340/517; 235/380; 250/473.1; 250/472.1

(58) Field of Classification Search ............... 340/540, 340/517, 521, 10.1, 385.1; 702/188, 30, 702/19; 73/31.05, 23.34, 53.05, 23.4; 235/380, 235/375, 382; 250/395, 473.1, 474.1, 336.1, 250/472.1
See application file for complete search history.

(56) References Cited

U.S. PATENT DOCUMENTS

| | | | | |
|---|---|---|---|---|
| 4,975,222 A | * | 12/1990 | Yoshino et al. | 252/586 |
| 5,722,835 A | * | 3/1998 | Pike | 434/218 |
| 7,109,859 B2 | * | 9/2006 | Peeters | 340/539.11 |
| 7,271,720 B2 | * | 9/2007 | Tabe | 340/540 |
| 7,491,948 B2 | * | 2/2009 | Gordon et al. | 250/472.1 |
| 7,522,040 B2 | * | 4/2009 | Passmore et al. | 340/540 |
| 2002/0024450 A1 | | 2/2002 | Townsend et al. | |
| 2003/0143119 A1 | | 7/2003 | Schwartz et al. | |

(Continued)

FOREIGN PATENT DOCUMENTS

DE 4322274 A1 1/1995

(Continued)

OTHER PUBLICATIONS

"Explosives and Narcotics Detection," retrieved off internet http://www.geindustrial.com/ge-interlogix/iontrack/prod_tech_overview.html on Dec. 2, 2005, 1 page.

"Explosives and Narcotics Detection—StreetLab," retrieved off Internet http://www.geindustrial.com/ge-interlogix/iontrack/prod_streetlab.html on Dec. 2, 2005, 1 page.

(Continued)

Primary Examiner — Toan N Pham
(74) Attorney, Agent, or Firm — Kilpatrick Townsend & Stockton LLP (57) ABSTRACT

A smartcard or other media detects the presence of chemical, biological, radiation, and/or explosive (CBRE) compounds or other items of interest on individuals handling the smartcard or other media. The exposure is stored such that, when the card is presented to a reader, the detection data is transmitted to the reader for appropriate processing by the system. In one embodiment, this invention provides a detection methodology which captures the fact that the holder of the detection device has been in contact with an item of interest without external power. The detector card is then able to alert appropriate authorities of that exposure when the device is presented to a reader in the normal course of the holder's business.

29 Claims, 9 Drawing Sheets

U.S. PATENT DOCUMENTS

2004/0204915 A1* 10/2004 Steinthal et al. ............ 702/188
2005/0022581 A1 2/2005 Sunshine
2006/0290496 A1 12/2006 Peeters
2007/0102294 A1 5/2007 Dorisio et al.

FOREIGN PATENT DOCUMENTS

| WO | WO 2004/114242 A1 | 12/2004 |
| WO | WO2006/035392 A1 | 4/2006 |
| WO | WO 2006/096246 A1 | 9/2006 |
| WO | WO20006/130528 A1 | 12/2006 |
| WO | WO 2007/081922 A2 | 7/2007 |

OTHER PUBLICATIONS

"Explosives and Narcotics Detection—Itemiser[3]" retrieved off internet http://www.geindustrial.com/ge-interlogix/iontrack/prod_itemiser.html on Dec. 2, 2005, 1 page.

"Explosives and Narcotics Detection—VaporTracer[2]" retrieved off internet http://www.geindustrial.com/ge-interlogix/iontrack/prod_vaportracer.html on Dec. 2, 2005, 1page.

"Explosives and Narcotics Detection—Entry Scan[3]" retrieved off internet http://www.geindustrial.com/ge-interlogix/iontrack/prod_entryscan.html on Dec. 2, 2005, 1 page.

* cited by examiner

SMART CARD DETECTORS

This application is a non-provisional of: U.S. Provisional Patent Application No. 60/938,677, filed May 17, 2007 for "SMART CARD DETECTORS" which is incorporated by reference in its entirety for all purposes. Further, this application is a non-provisional of: U.S. Provisional Patent Application No. 60/949,228, filed Jul. 11, 2007 for "MULTI-MODAL SMARTCARD DETECTION AND REPORTING OF CHEMICAL, BIOLOGICAL, RADIATION, AND EXPLOSIVE MATERIAL."

BACKGROUND OF THE INVENTION

This disclosure relates in general to chemical, biological, radiation and explosive detection and, but not by way of limitation, to smartcard detection.

Detection of trace particles or emanations from compounds which may represent a threat to the public is based on the capture and analysis of the material. Capture may be accomplished through contact (e.g., wipe a surface or contact with a capture surface) or through capture from the atmosphere (e.g., forced air flow such as a "puffer" to dislodge particles from surfaces or through vapor sampling from the atmosphere).

Analysis in most current systems employs ion mobility spectroscopy as the mechanism for detecting items of interest. The detection capture and analysis devices may be installed in the infrastructure being protected such as at the portals for entry or exit, positioned to capture from the persons involved through contact (e.g., touch or swipe) or may be handheld and employed by those protecting the infrastructure. Such devices are common in airports today. The devices typically are slow in the capture and analysis process, frequently require operator participation and require regular cleaning, potentially after each use. In addition, the analysis results are frequently ambiguous, resulting in high false alarm rates.

An emerging class of detection devices relies on the capture of the threat indicating material causing a change in the composition of the material of the device which captures it. The change is then observable or causes a detectable change in the reflective photo luminescence. For example, film tags are used in nuclear facilities to determine if there has been exposure to radiation. Optical scanners may be employed to detect the change in luminescence when the capture material is presented. In cases where the change in the capture material is visible, the holder may dispose of the device before the capture event is recorded.

BRIEF SUMMARY OF THE INVENTION

One embodiment detects the presence of chemical, biological, radiation, and/or explosive (CBRE) compounds or other items of interest on individuals handling smartcards or other media. The exposure is stored such that, when the card is presented to a reader, the detection data is transmitted to the reader for appropriate processing by the system. In one embodiment, this invention provides a detection methodology which captures the fact that the holder of the detection device has been in contact with an item of interest without external power. The detector card is then able to alert appropriate authorities of that exposure when the device is presented to a reader in the normal course of the holder's business. In one embodiment, the detection state is not visible to the individual holding and/or presenting the device.

In one embodiment, a detector card for recording exposure to an item of interest is disclosed. The detector card includes a media, an antenna, a power source, an electronic circuit and a material. The antenna sends exposure information and is embedded in the detector card. The power source inductively couples energy into the detector card. The electronic circuit embedded in the media is wirelessly readable. The material reacts when exposed to the item of interest. The electronic circuit can detect if the material has reacted.

In another embodiment, a detection media for recording exposure to an item of interest is disclosed. The detection media includes a media, an antenna, a power source, an electronic circuit, and a sensor. The antenna sends exposure information to a reader, for example. The electronic circuit is embedded in the media and is wirelessly readable. The sensor reacts when exposed to the item of interest. The electronic circuit can determine if the sensor has reacted and relay exposure information.

In yet another embodiment, a method for detecting items of interest with a detection media is disclosed. In one block, exposure to an item of interest is sensed to create exposure information. The exposure information is stored. An electronic circuit of the detection media is powered without a wired power source. The exposure information is wirelessly read from the detection media.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

In one embodiment, a chemiselective or detection polymer captures trace particles or emanations from a specific threat compound. A conductive polymer senses the change in a characteristic of the detection polymer after the capture of the target particle or emanation. The exposure information is transferred to the electronic circuit embedded in the smartcard or token. The electronic circuit wirelessly communicates with a reader in a manner consistent with the present or future reader standards.

In another embodiment, a smartcard or smart token is used for access control or security systems operating at 13.56 MHz or higher with the ability to detect and report trace CBRE material that has been in contact with the smartcard or token. Other embodiments could use any monetary instrument, ticket, card, contactless, RFID, or token used for access and/or payment. When the card communicates with any type of Automatic Fare Collection system such as those found in, public transportation systems, automated parking systems, stadium event ticketing systems or building access systems, the trace detection status of what has come in contact with the smartcard is reported through the infrastructure in order to provide detection, intelligence gathering information, and prevention of terrorist incidents. This information may be used for intelligence collection into a special situational awareness software program or interface into a command and control (C2) or communication, command and control (C3) system.

A smartcard, token or portable detector using a polymer sensor technology, such as but not limited to, fluorescent quenching or molecularly imprinted polymer (MIP) technology that can register detection of a substance that has come in contact with the card or token when in an powered or non-powered state. These technologies interact with an additional conductive polymer and/or nanotechnology layer(s). The detection polymer and the conductive polymer or nanotechnology may be amalgamated or conjunctively combined. When the detection polymer is contaminated with item of interest, it interacts with the other polymer materials, and a signal is generated and relayed to a microprocessor or memory cell located in a smartcard. The interaction can be through a chemical, physical, or electronic change. The change signifies that a detection of a target substance or substances has occurred. The detection event triggers changes in an electrical or data characteristic of the smartcard that corresponds to the specific sensors targeted triggering substance. Each card can have one or many detection sensor inputs and can be configurable to accept combinations of any CBRE substances.

The detector card or token has two basic configurations, one which incorporates an integral power source and the second which is powered when it is placed within the electromagnetic field generated by a reader. Each configuration has the ability to detect trace materials (vapors, emanations or particles) associated with a known compound that is or may be representative of an item of interest. Embodiments of the invention detect the trace material(s) and report it wirelessly to the reader to deter, prevent or contain the potential threat should it be validated. In addition to being able to detect the item of interest, some embodiments also provide an indication of the volume or strength of trace materials detected.

Detection polymers exist for most explosive and chemical threat agents. Additionally, materials can capture radiation emanations and polymers for biological material. Embodiments of the invention can contain one or multiple polymers for detection (e.g., fluorescent quenching or MIP) and one or multiple polymers and nanotechnologies for conducting signals to the electronic circuitry. These two types of polymers can be amalgamated or conjunctively joined into a card substrate. Carbon nanotubes and other nanotechnology can be used for printed electronic circuits and to interface with the conducting polymer. The application of the polymers, combined in either a mixed or a layered scheme can be applied using multiple methods, as a polymer/nanotech ink, using a spray method, brushing, spin-coating, printing, and/or roller-coating. Ink jet printing technology can be used, for example, to spray apply the polymer(s) and form nanotech circuits on or in the surface or substrate materials. This embodiment is in the form of a smartcard that transfers the detection event data to the reader employing standard smartcard communication methods.

A smartcard is used by individuals in a number of applications that are germane to this invention. A smartcard may be of a contact or contactless type in various embodiments. In a contact type, the chip is read when physical contact is made on the electrical interface pads for the chip. A contactless card is read wirelessly at a distance. Some embodiments could have multiple wired or wireless smartcard circuit completely separate from the detection circuitry rather than integrating the two functions as in this embodiment. An embodiment can be a smartcard with a built-in battery. The detector card may be a token or credential (e.g., badge, ID card, license, etc.), a bank card (e.g., credit, debit, stored value, etc.), or a preferred customer or member card or a prepaid card for other economic applications (e.g., transit system fares, NFC enabled cellular phone, prepaid gift cards, etc.). The detector card or media fits within the palm of a human hand, but other embodiments could be less than 10, 8, 6, 5, 4, 3, 2, or 1 $in^2$ and thinner than 10, 8, 6, 5, 4, 3, 2, or 1 mm.

Currently available are a class of conductive polymers that have conductivity levels between those of semiconductors and metals. Until recently, these conductive polymers did not have sufficient conductive properties to be utilized in manner of this invention. Conductive polymers, such as but not limited to, the highly conductive Clevios™ series available HS Starck™ that provides the base material for an electrical conversion for the detection polymer (e.g., MIP).

The combination of the detection polymer with a conductive polymer provides the basic component used in a sensor that can detect and have an electrical property change that can be electronically relayed. The combination of the two polymers is performed as an amalgamated polymer or a conjunctively combined polymer. The currently commercially available conductive polymers have a conductivity rating up to 1500 ohms/$cm^2$ that allows for an electromagnetic field to provide enough induced power to quantify an electrical characteristic change in the detection polymer. This change will occur when the detection polymer moves from an uncontaminated to a contaminated state.

Nanotechnology techniques, such as but not limited to, carbon nanotubes, can be used to form the circuit that can discriminate the signals generated from the contaminated detection polymers. The electrical signals can be developed through changes in inductive coupling, capacitive coupling, magnetic coupling or resistivity.

Figure 1:
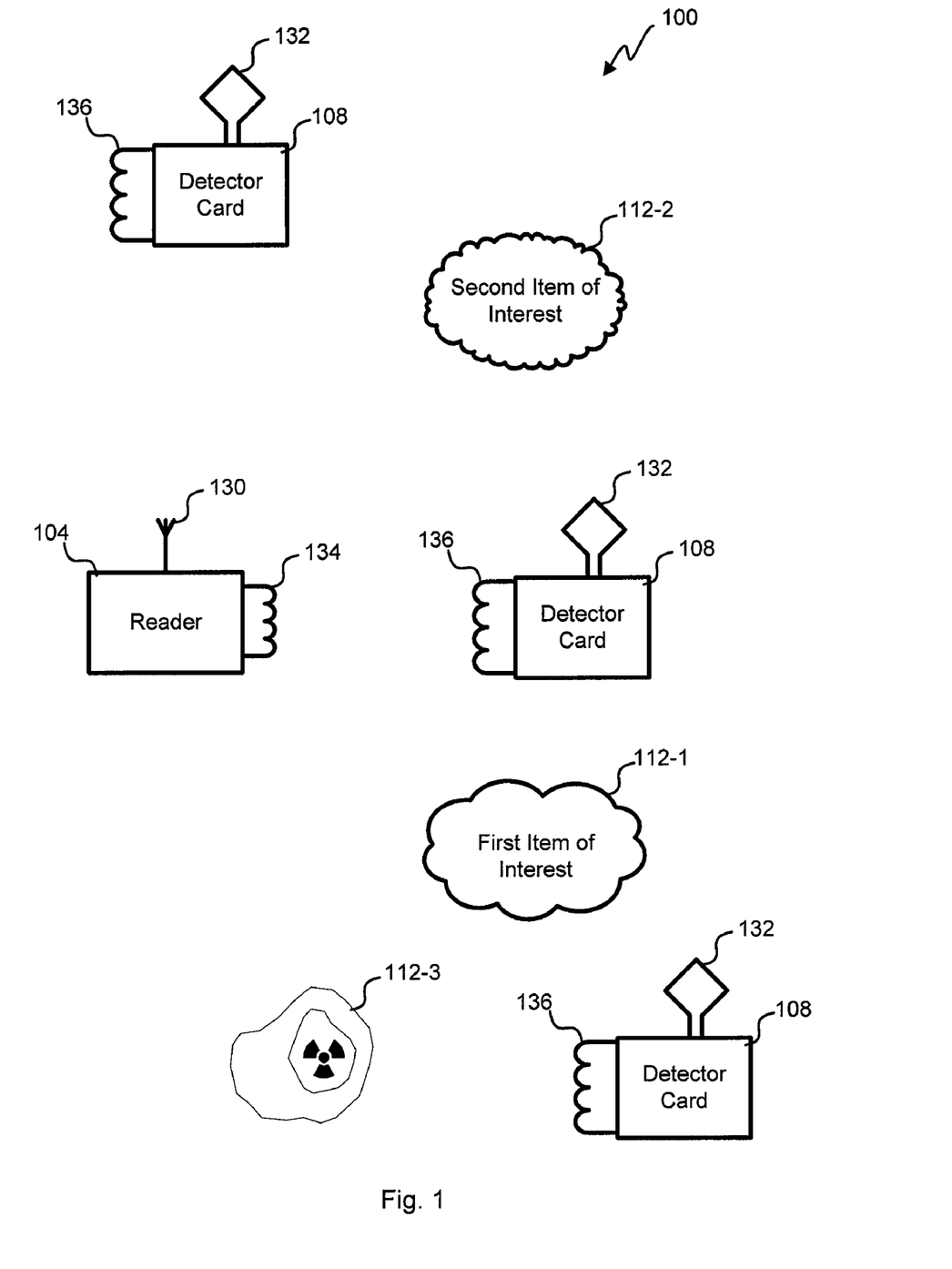
FIG. 1 depicts a block diagram of an embodiment of a detection system in an environment of items of interest.

Referring initially to FIG. 1, a block diagram of an embodiment of a detection system 100 in an environment of items of interest 112 is shown. This embodiment has several detector cards or media 108 that each communicate with an antenna 132 and receive power inductively through a coil 136. The detector media 108 are exposed to various items of interest 112 as they travel with an associated user. The detector media 108 are capable of sensing exposure to one or more items of interest, even when the coil 136 is not receiving power. Any exposure can be communicated as detection information to a reader or reader 104.

The detector cards or media 108 communicate with readers using wireless radio frequencies (RF), for example, 13.56 MHz or higher frequency signals could be used. The detector card 108 or token could be used as a smartcard for other purposes. For example, the detector card 108 could be used for access into a system such as, public transportation systems, automated parking systems, stadium event ticketing systems or building access systems. Additionally, the detector card 108 could be part of a phone or credit or debit card. The detector media 108 need not be in card form and can be any type of RF identification (RFID).

At any time, a reader 104 can wirelessly power a detection media 108 and communicate with the detector media 108 within communication range. Readers 104 could be handheld or fixed, but can read any detection information in nearby detector media 108 from a distance. The reader uses a coil 134 to send power to the detector media 108. An antenna 130 of the reader 104 is used to communicate with the detector media 108.

Various items of interest 112 can be sensed by the detector card 108. The items of interest could be a chemical, a biologic compound, radiation, and/or an explosive (CBRE), for example. As the detector card 108 is carried by the user, any exposure to these items of interest 112 can be sensed and that information retained in some manner until a reader 104 reads the information. The item of interest may be directly transferred by contact or indirectly without any contact.

Figure 2A:
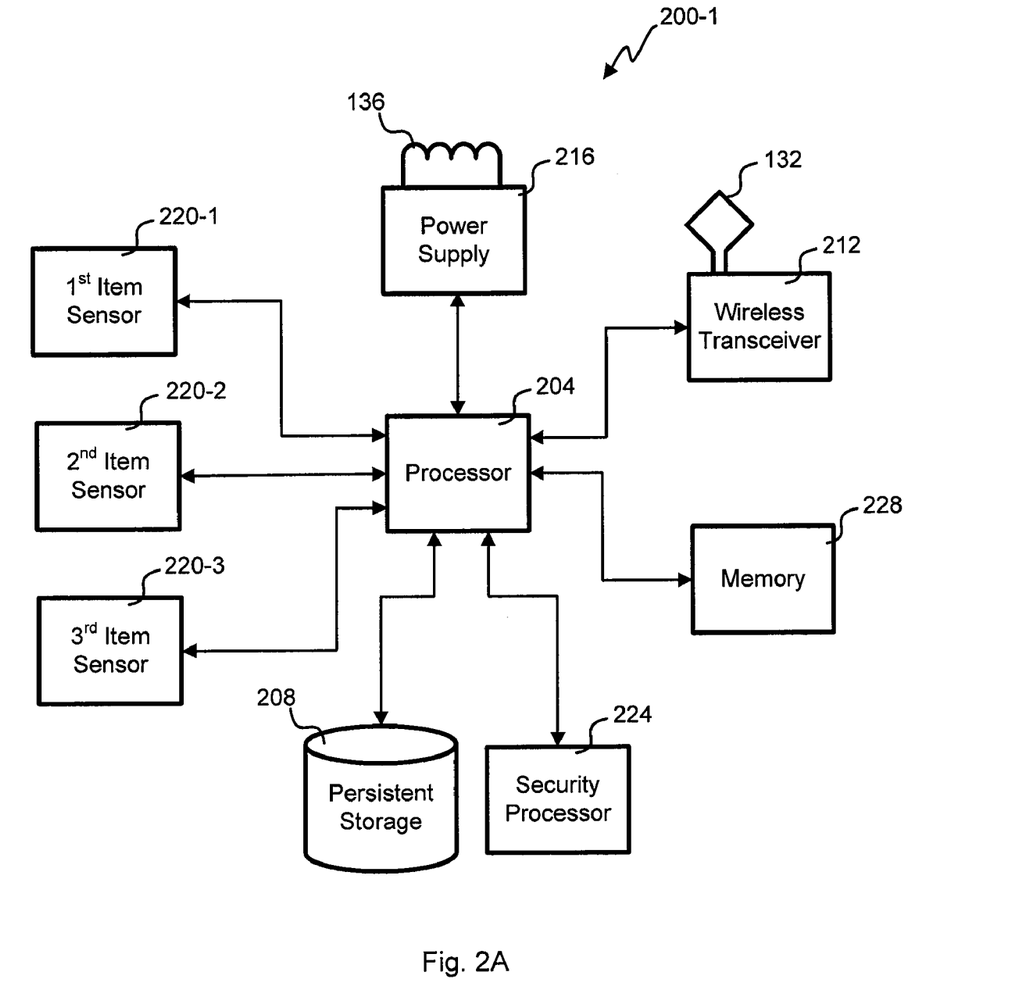
FIGS. 2A and 2B depict block diagrams of embodiments of a wireless detector circuit.

With reference to FIG. 2A, a block diagram of an embodiment of a wireless detector circuit 200-1 is shown. The detector circuit 200-1 is embedded in a detector card 108 in this embodiment, but could be embedded into anything. A processor 204 or microcontroller runs software using the memory 228. The software can be held in the persistent storage 208 such as flash, ROM or some other non-volatile memory. The persistent storage 208 can be used to store identifiers for the wireless detector circuit 200-1 and sensor readings. Various amounts of historical sensor readings can also be stored in the persistent storage 208.

This embodiment of the detector card 108 is used as a smartcard. A security processor 224 can be used for authentication, authorization or secure storage of information. Other embodiments could be used for no more than sensing items of interest without the other smartcard functionality. Some embodiments could have a separate wired or wireless smartcard circuit completely separate from the detection circuitry rather than integrating the two functions as in this embodiment.

A wireless transceiver 212 allows bi-directional communication with the wireless detector circuit 200. The antenna 132 is used for this communication. Other embodiments could have multiple transceivers and antenna tuned to other frequencies and/or configured to work with other standards. Some embodiments could have only transmission capability in the wireless detector circuit 200.

A power supply 216 allows intermittent energy supply to the wireless detector circuit 200. When in range with a reader 104, energy is coupled to the coil 136 and converted into appropriate voltages by the power supply 216. The wireless detector circuit 200 becomes fully functional when properly energized by the reader 104.

This embodiment has passive sensors 220 that do not require power to record exposure to items of interest. For example, fluorescent quenching polymers or molecularly imprinted polymer (MIP) technology can report detection of a substance that has come in contact with the item sensor 220 when the wireless detector circuit 200 is in an powered or non-powered state. The item sensor 220 can read a chemical, physical, or electronic change in the MIP. The change signifies that a detection of a target substance or substances has occurred. Each item sensor 220 can be configured to be sensitive to one or more compounds or conditions.

When the wireless detector circuit 200 is next powered, the exposure of the detection polymer can be recorded in the persistent storage 208 as exposure information. The value of the exposure information can be a value indicative of the amount of exposure experienced. The characteristics of the detection polymer can be such that the resistance (or some other electrically readable characteristic) changes as a function of exposure.

Figure 2B:
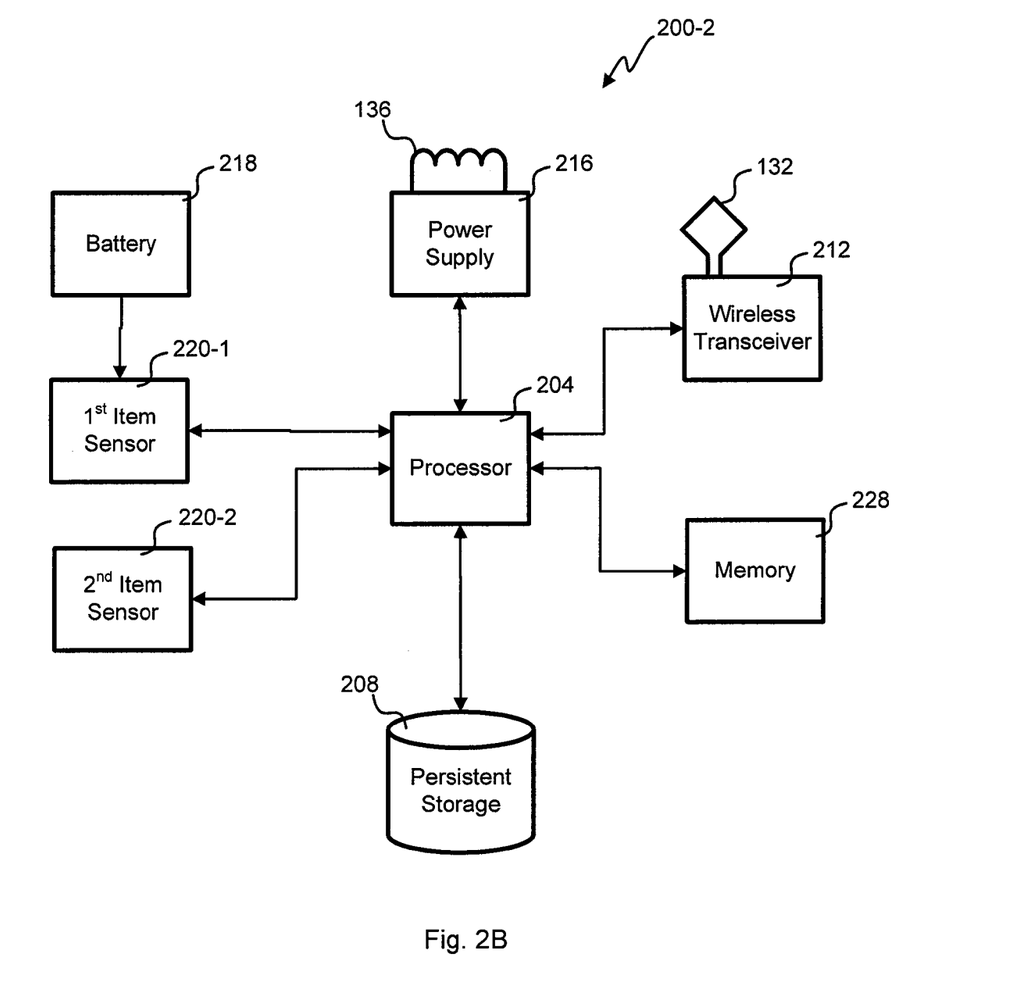

Referring next to FIG. 2B, a block diagram of another embodiment of a wireless detector circuit 200-2 is shown. This embodiment doesn't include the security processor 224. The wireless detector circuit 200 has two item sensors 220. The second item sensor 220-2 reacts with one or more items of interests without requiring power. The first item sensor 220-1 uses battery power to detect one or more items of interest. The battery 218 can be used by the first item sensor 220-1 to detect and/or hold the exposure information. Other embodiments could use the battery 218 for other parts of the wireless detector circuit 200-2 to store the exposure information in the persistent storage 208, for example.

Figure 3A:
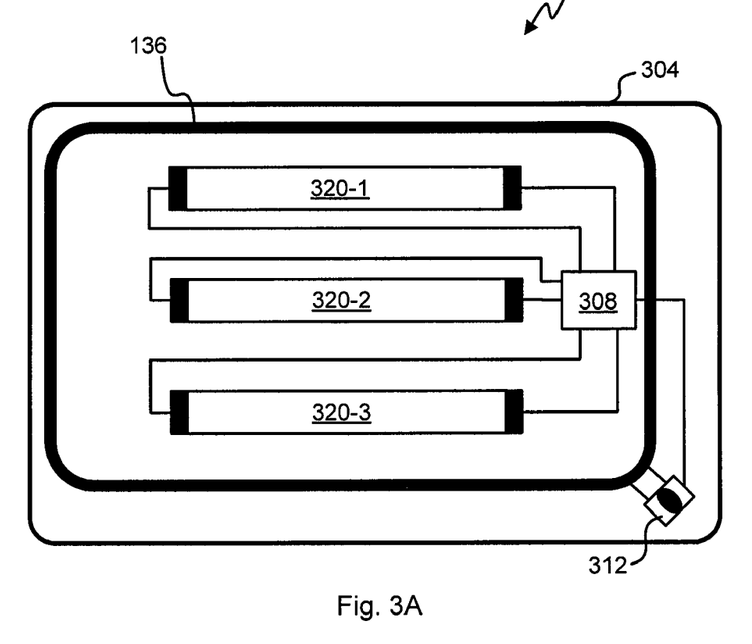
FIGS. 3A and 3B depict diagrams of embodiments of a detector card.

With reference to FIG. 3A, a cross-sectional diagram of an embodiment of a detector card 108 is shown. Various items are embedded into a media 304, which could be made from plastic, for example. This embodiment has three item sensors 320 that change resistivity with a detection polymer. The resistance is measured by sensor electronics 308 and reported back to an embedded chip or integrated circuit (IC) 312 for recording the exposure information. The embedded chip could include memory 228, a processor 204, a security processor 224, persistent storage 208, a wireless transceiver 212, and a power supply 216.

Figure 3B:
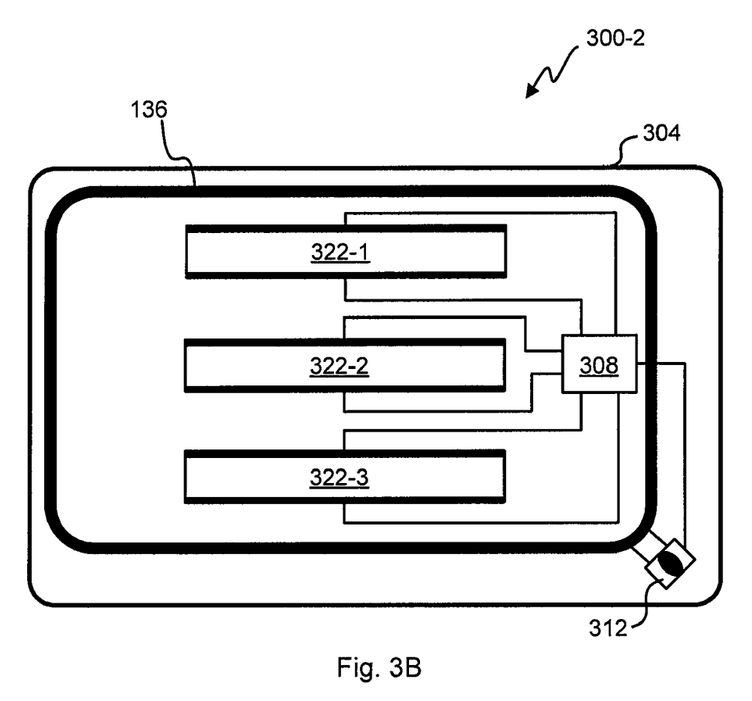

Referring next to FIG. 3B, a cross-sectional diagram of another embodiment of a detector card 108 is shown. This embodiment has three item sensors 322 that are configured differently from the embodiment of FIG. 3A to measure changes in capacitance. Various embodiments of the item sensors 322 could change inductance, magnetism, resistance, capacitance, opaqueness, etc. Generally, the detection polymer changes the electrical characteristics of item sensors 322 as a function of exposure to an item of interest 112. The detection polymer binds with the item of interest during exposure.

Figure 4A:
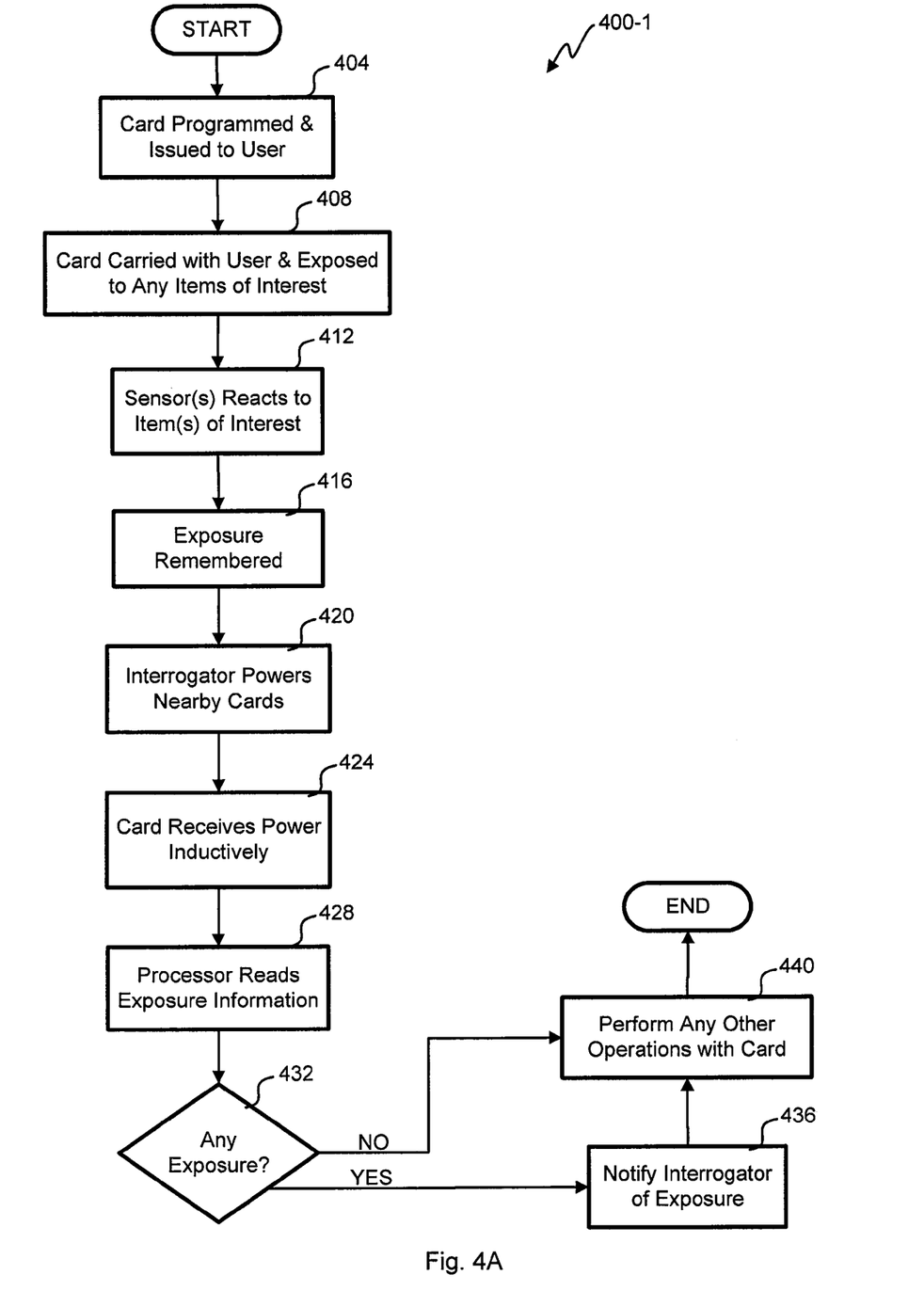
FIGS. 4A and 4B illustrate flowcharts of embodiments of a process for detecting items of interest with a detector card.

With reference to FIG. 4A, a flowchart of an embodiment of a process 400-1 for detecting items of interest with a detector card 108 is shown. The depicted portion of the process 400-1 begins in block 404 where the detector card is issued to a user along with any programming. For example, the detector card 108 could be written with user information, applications, user preferences, serial numbers, and/or other information. The user carries around the detector card 108 where it potentially is exposed to items of interest in block 408.

In block 412, the item sensor 220 reacts to exposure to the relevant item(s) of interest. Any exposure is remembered as exposure information in block 416. The exposure information may be stored in the sensor material using a detection polymer, for example, or some other material sensitive to the item(s) of interest.

At some point, the detector card 108 comes in contact with a reader 104 in block 420 that powers the coil 136 of the detector card 108 to power up the detector circuit 200 in block 424. The processor 204 reads one or more item sensors 220 in block 428. The detection polymer remembers the exposure that can be read at any time as exposure information. The exposure information could be a range of values.

Where there is exposure detected in block 432, the reader 104 is sent the exposure information wirelessly in block 436. Processing continues from block 436 to block 440 where any other operations are performed with the detector card 108. Where exposure hasn't been detected, processing goes from block 432 to block 440 to perform any other operations with the detector card 108 that the reader 104 might perform.

Figure 4B:
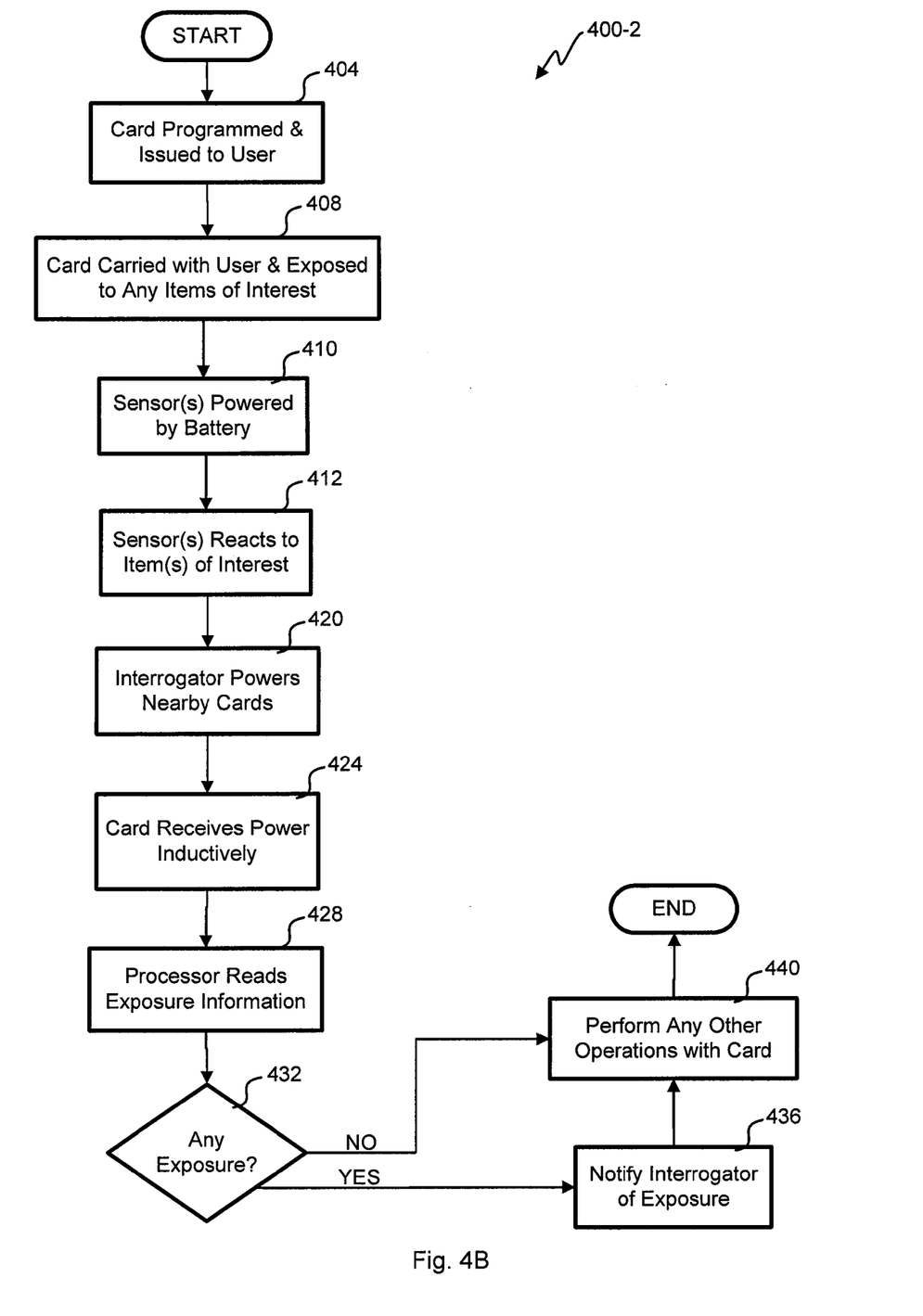

Referring next to FIG. 4B, a flowchart of another embodiment of a process 400-2 for detecting items of interest with a detector card 108 is shown. This embodiment uses a battery 218 in block 410, which differs from the embodiment of FIG. 4A in that block 410 is inserted between blocks 408 and 412. The battery powers one or more item sensors 220 while in the field. Gathered exposure information is stored for later readout. The remaining blocks of the process 400-2 are the same as FIG. 4A.

Figure 5A:
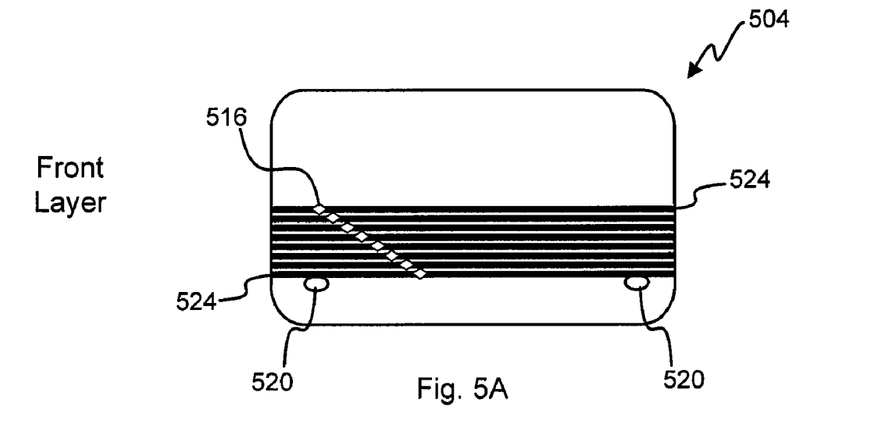
FIGS. 5A, 5B and 5C depict a structural diagram of an embodiment of the detector card having three layers of construction.
Figure 5B:
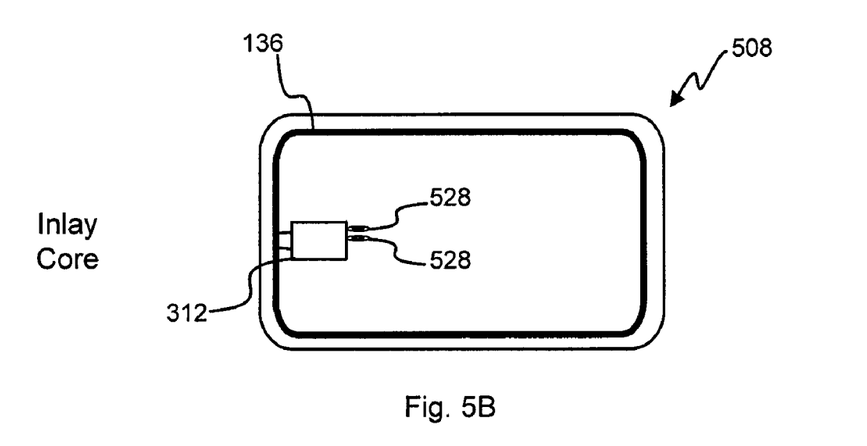
Figure 5C:
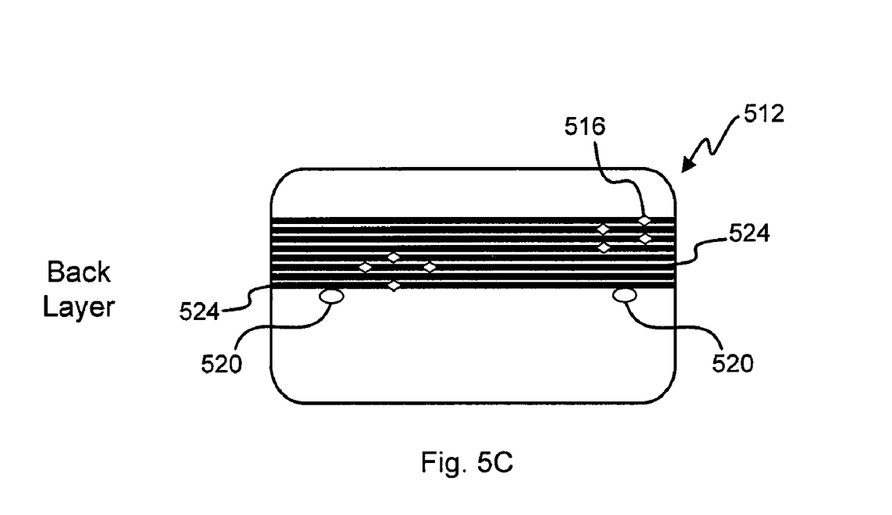

Referring next to FIGS. 5A, 5B and 5C, a structural diagram of an embodiment of the detector card having three layers of construction is shown. The configuration can be changed dependent upon the requirements of the media that the polymers will be embedded and the ergonomics of the device to enhance detection from the expected handling of the detector card. The front and back layers 504, 512 are made of a plastic, plasticized, polyvinyl or paper material in which various layers of amalgamated, aggregated, or conjunctively combined conductive polymers 520 and detection polymers 524 are applied in an interlaced or checkered pattern, for example. This pattern can vary with ergonomic requirements.

Each of these detection polymer stripes 524 are integrated with a sensor 516 that transfers the conductivity change in value to the inner layer or inlay core 508 using sensor connection points 528. The inlay core 508 processes the sensor information and acts as a transmitter to either the integrated circuit (IC) 312 or printed circuit (PC) contact point, which could include the use of the existing antenna inputs. A method of detuning the antenna may be implemented as well when the detection polymer changes in characteristics due to a threat substance exposure. The change in characteristics of the detection polymer may be inductive, voltage, resistance, and conductive and/or magnetic in nature.

The IC or PC 312 will evaluate the change in input characteristics during and when a detection change occurs, or simply reacts to the change in antenna Q factor and or both to trigger the IC or PC 312 to take the appropriate action to signal that a detection occurrence took place. In turn, the smartcard reader (or PCD) 104 interrupts this change in signal detection and transmits or sends the appropriate information to the host processing system for a valid response.

Figure 6A:
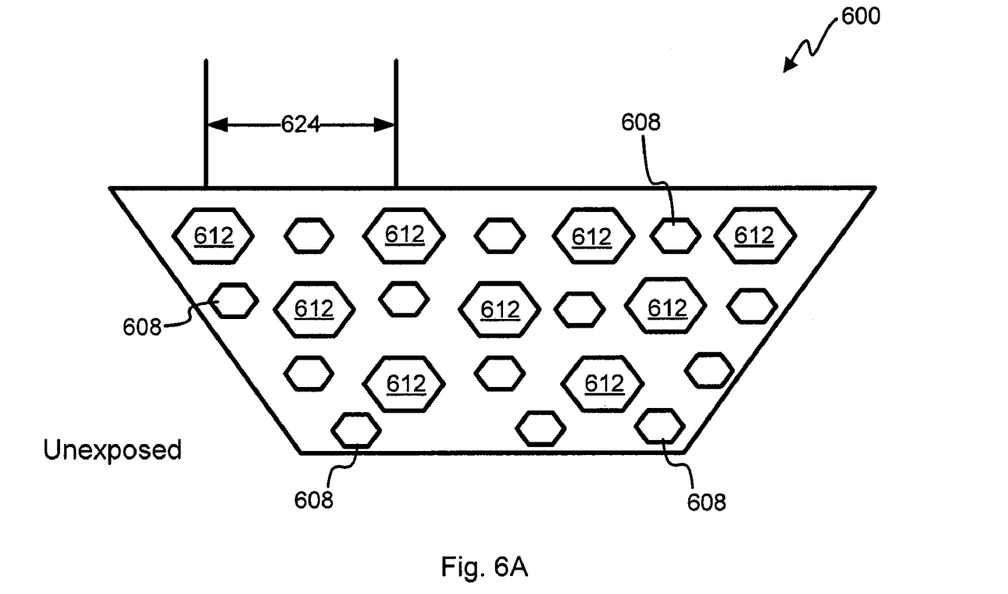
FIGS. 6A and 6B depict diagrams of an embodiment of detection and conduction polymer before and after detection.
Figure 6B:
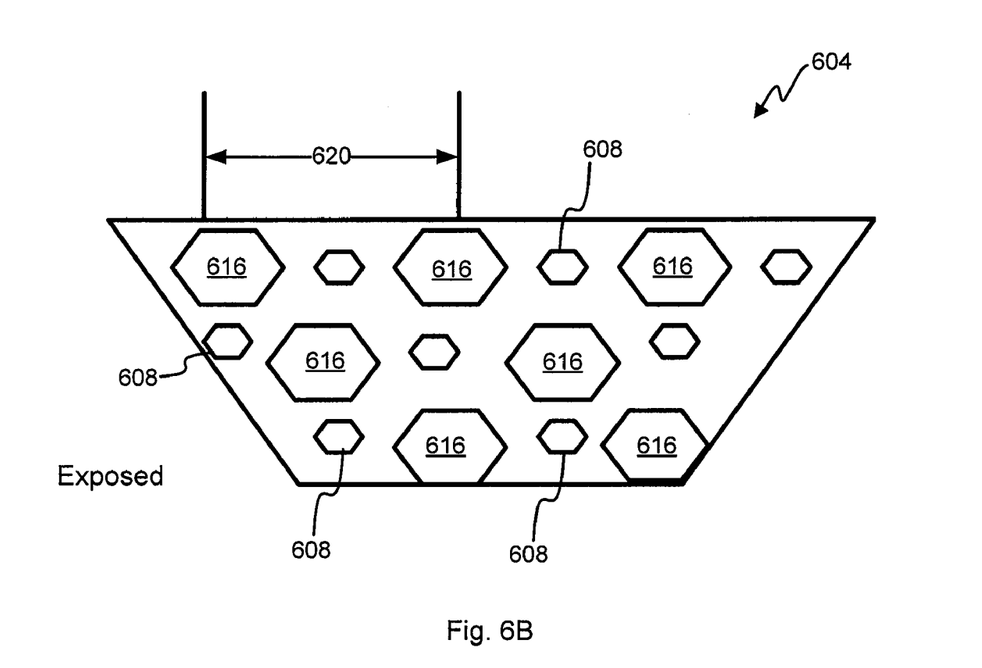

Referring next to FIGS. 6A and 6B, a diagram of an embodiment of detection and conduction polymer is shown both before 600 and after detection 604. In this embodiment, the detection and conduction polymers are mixed or interspersed. The polymer materials being applied to the detector card include two types of base polymers that include a conductive polymer 608 and the other a chemical, biological, radiological or explosives detection sensitive polymer 612, 616. The unexposed detection polymer 612 is shown in FIG. 6A and the exposed detection polymer 616 is shown in FIG. 6B. In this example, the detection polymer 612, 616 changes the state of the conductive polymer 608 by decreasing or increasing the conductivity of the conductive polymer 608.

In this embodiment, the spacing relationship between the conductive polymer 608 and the detection polymer 612 is a known distance yielding a known value of conductivity measured in ohms/cm$^2$. The distance between the conductive polymer particles or monocles will increase resulting in an ohmic value increase, or the conductivity will decrease when the detection polymer 612, 616 is subjected with a threat substance in which the detection polymer 612, 616 is designed to respond. The smaller distance 624 is shown in FIG. 6A and the larger distance 620 is shown in FIG. 6B.

As the detector card 108 is carried and handled by the user any item of interest (CBRE particulates or vapors) will cause the unseen reaction in the detection polymer 612, 616 and the event will either be stored or set for reading when external power is applied to the detector card 108. In the embodiment of a detector card that contains a power source, the event can be detected and read once the detection polymer 612, 616 has provided a large enough change of electrical properties such that it can be measured by the microprocessor or IC 312. There are various embodiments to demonstrate how the polymers can be arranged and methods of deposition onto a card, ticket or other surface.

Figure 7:
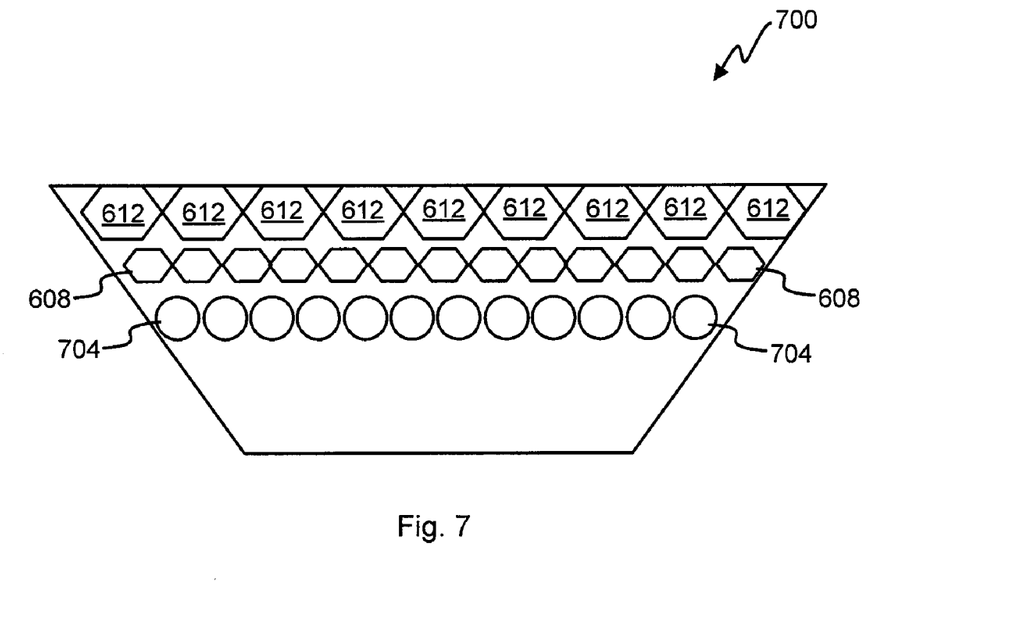
FIG. 7 depicts a diagram of an embodiment of a layered polymer configuration for a sensor.

Referring next to FIG. 7, an embodiment of a layered polymer configuration for a sensor is shown. This embodiment demonstrates how the polymers can be combined conjunctively, in a layered manner. In this embodiment, the detection polymer is not mixed with the conductive layer as in the embodiments of FIGS. 6A and 6B, but is applied after the conductive layer is dried or cured.

When the detection polymer 612 is exposed to the particulates or vapors of interest, a change in the detection polymer 612 allows the conductive polymer 608 and nanotechnology layer 704 to read that change. This reading is based on changes of resistance, capacitance, magnetic coupling or inductive coupling that can occur when the detection polymer 612 is contaminated with a specific item of interest such as a particular explosive material component, a chemical material component, or a radiation component, or biological contamination.

This signal is stored and forwarded into an IC and/or hosting system. This process can occur in real time when the detection device is one that incorporates its own power supply or in the case of a smartcard application it would occur during the initial communication phase with a smartcard reader.

The smartcard reader can be a portable unit or one that is mounted in a permanent or semi-permanent location. In this embodiment, the detection polymer(s) 612 can be more than one selectively sensitive polymer applied in a bar code type of arrangement that would allow for the detection of multiple specific items of interest. The electrical change sensor would be connected to the multiple areas of each specific polymer to allow for the identification of the specific item of interest that was detected.

Other physical devices such as key fobs and cell phones may also have this conductive polymer applied to allow detection of items of interest. The application of the polymers, combined in either a mixed or a layered scheme can be applied using multiple methods, as a polymer/nanotech ink, using a spray method, brushing, spin-coating, printing, and/or roller-coating. Ink jet printing technology can be used, for example, to spray apply the polymer to the surface or substrate.

Detection polymers are polymers that are currently available to detect a particular item of interest. They could include vapor or particulate sensing polymers, florescent quenching polymers, and/or Molecularly Imprinted Polymers (MIP). Current classifications of sensing would include Chemical, Biological, Radiation and Explosive (CBRE). The molecular formula and the electrical properties for each classification of substances vary, as well as the formulations for each subclass. For example; the molecular formula for a MIP polymer that detects TNT will vary from the molecular formula for the MIP polymer that detects RDX. These differing formulas cause the electrical properties, conductance or resistance, of each formulation to typically be different.

Each detection polymer type is matched with a specific formulation of conductive polymer and/or nanotechnology particulates, such that a electrical signature can be read once it is exposed to the specific analyte that causes the positive chemical reaction in the chemi-selective detection polymer. The value of the exposure information can be a value indicative of the amount of exposure experienced. The characteristics of the MIP can be such that the resistance (or some other electrically readable characteristic) changes as a function of exposure.

A number of variations and modifications of the disclosed embodiments can also be used. For example, many embodiments discuss use of a smartcard or card. The invention is not meant to be so limited and could be embedded into automobile parts, handbags, shoes, belts, other clothing, hats and helmets, weapons, equipment, laptops, cooking utensils, cell phones, inventory, shipping boxes and containers, or any other portable items. Embodiments could be embedded into any human-transported item. The above embodiment describe use with a contactless smartcard, but other embodiments could use a smartcard with contacts.

While the principles of the disclosure have been described above in connection with specific apparatuses and methods, it is to be clearly understood that this description is made only by way of example and not as limitation on the scope of the disclosure.

What is claimed is:

1. A detector card for recording exposure to an item of interest, the detector comprising:
   a media;
   an antenna for sending exposure information, wherein the antenna is embedded in the detector card;
   a power source that inductively couples energy into the detector card;
   an electronic circuit embedded in the media, wherein the electronic circuit is wirelessly readable; and
   a material that reacts when exposed to the item of interest, wherein the electronic circuit can detect if the material has reacted.

2. The detector card for recording exposure to the item of interest as recited in claim 1, wherein the material comprises molecularly imprinted polymer(s).

3. The detector card for recording exposure to the item of interest as recited in claim 1, wherein the material comprises fluorescent quenching polymer(s).

4. The detector card for recording exposure to the item of interest as recited in claim 1, wherein the material is formed with a detection polymer(s) and a conducting polymer(s).

5. The detector card for recording exposure to the item of interest as recited in claim 1, wherein the material comprises a plurality of layers conjunctively formed with detection polymer(s) and conductive polymer(s).

6. The detector card for recording exposure to the item of interest as recited in claim 1, wherein the material comprises a plurality of layers of an amalgamated polymer formed with a detection polymer(s) and a conductive polymer(s).

7. The detector card for recording exposure to the item of interest as recited in claim 1, wherein the material comprises a plurality of layers conjunctively formed with a detection polymer(s), a conductive polymer and nanotechnology.

8. The detector card for recording exposure to the item of interest as recited in claim 1, wherein the material comprises a plurality of layers of an amalgamated polymer formed with a detection polymer(s), a conductive polymer(s) and nanotechnology combination.

9. The detector card for recording exposure to the item of interest as recited in claim 1, wherein the material is applied in an ink form to the media.

10. The detector card for recording exposure to the item of interest as recited in claim 1, further comprising a second material that reacts when exposed to a second item of interest, wherein the electronic circuit can detect if the second material has reacted.

11. The detector card for recording exposure to the item of interest as recited in claim 1, wherein the material is reactive to a chemical, a biologic compound, radiation, and/or an explosive.

12. The detector card for recording exposure to the item of interest as recited in claim 1, wherein a state of the material after reaction is not visible to the unaided human eye.

13. The detector card for recording exposure to the item of interest as recited in claim 1, wherein the detector card is a wireless smartcard.

14. The detector card for recording exposure to the item of interest as recited in claim 1, wherein the detector card is a contact smartcard.

15. The detector card for recording exposure to the item of interest as recited in claim 1, further comprising a battery that aids the material in sensing the item of interest.

16. A detection media for recording exposure to an item of interest, the detection media comprising:
    a media;
    an antenna for sending exposure information;
    a power source at least partially powered wirelessly using induction;
    an electronic circuit embedded in the media, wherein the electronic circuit is wirelessly readable; and
    a sensor that reacts when exposed to the item of interest, wherein the electronic circuit can determine if the sensor has reacted and relay exposure information.

17. The detection media for recording exposure to the item of interest as recited in claim 16, wherein the power source comprises a coil that inductively couples power to the electronic circuit.

18. The detection media for recording exposure to the item of interest as recited in claim 16, wherein the sensor includes a polymer that transitions to different state when exposed to the item of interest.

19. The detection media for recording exposure to the item of interest as recited in claim 16, wherein the sensor is powered when sensing for the item of interest.

20. The detection media for recording exposure to the item of interest as recited in claim 16, wherein the sensor comprises a material that reacts without requiring power to the sensor.

21. The detection media for recording exposure to the item of interest as recited in claim 16, wherein the power source comprises a battery that couples power to the sensor.

22. The detection media for recording exposure to the item of interest as recited in claim 16, wherein the antenna is embedded in the media.

23. A method for detecting items of interest with a detection media, the method including steps of:
   sensing exposure to an item of interest to create exposure information;
   storing the exposure information;
   powering an electronic circuit of the detection media without a wired power source using induction; and
   wirelessly reading the exposure information from the detection media.

24. The method for detecting items of interest with the detection media as recited in claim 23, wherein the storing step comprises a step of storing with a reactive polymer.

25. The method for detecting items of interest with the detection media as recited in claim 23, wherein the storing step comprises a step of storing with electronic memory.

26. The method for detecting items of interest with the detection media as recited in claim 23, wherein the sensing step is performed without use of any power from the detection media.

27. The method for detecting items of interest with the detection media as recited in claim 23, wherein the sensing step uses a battery power source.

28. The method for detecting items of interest with the detection media as recited in claim 23, wherein the powering step comprises a step of receiving energy inductively.

29. The method for detecting items of interest with the detection media as recited in claim 23, wherein the powering step comprises a step of receiving energy from a battery.

* * * * *

UNITED STATES PATENT AND TRADEMARK OFFICE
CERTIFICATE OF CORRECTION

| | | |
|---|---|---|
| PATENT NO. | : 7,936,265 B2 | Page 1 of 1 |
| APPLICATION NO. | : 12/123387 | |
| DATED | : May 3, 2011 | |
| INVENTOR(S) | : Jon D. Macklin et al. | |

It is certified that error appears in the above-identified patent and that said Letters Patent is hereby corrected as shown below:

Please insert in section (60) on the face of the patent after "Provisional application no. 60/938,677, filed on May 17, 2007," the following in the priority section:

--and Provisional application no. 60/949,228, filed on July 11, 2007.--

Signed and Sealed this
Fifth Day of July, 2011

David J. Kappos
*Director of the United States Patent and Trademark Office*